US012629335B2

(12) United States Patent
Serrano Sanmiguel et al.

(10) Patent No.: US 12,629,335 B2
(45) Date of Patent: May 19, 2026

(54) CHITOSOMES OR CHITOSAN-COATED LIPOSOMES, USE THEREOF TO OBTAIN COSMETIC OR PHARMACEUTICAL COMPOSITIONS AND PREPARATION METHOD THEREOF

(71) Applicant: DERMOPARTNERS, S.L., Valencia (ES)

(72) Inventors: Gabriel Serrano Sanmiguel, Valencia (ES); Pilar Serrano Ballesteros, Valencia (ES); Eva Marti Civera, Valencia (ES); Silvia Mir Palomo, Valencia (ES)

(73) Assignee: DERMOPARTNERS, S.L., Valencia (ES)

( * ) Notice: Subject to any disclaimer, the term of this patent is extended or adjusted under 35 U.S.C. 154(b) by 255 days.

(21) Appl. No.: 18/551,990

(22) PCT Filed: Mar. 23, 2021

(86) PCT No.: PCT/ES2021/070201
§ 371 (c)(1),
(2) Date: Sep. 22, 2023

(87) PCT Pub. No.: WO2022/200640
PCT Pub. Date: Sep. 29, 2022

(65) Prior Publication Data
US 2024/0165028 A1    May 23, 2024

(51) Int. Cl.
| | |
|---|---|
| *A61K 8/14* | (2006.01) |
| *A61K 8/9741* | (2017.01) |
| *A61K 9/127* | (2025.01) |
| *A61K 9/1273* | (2025.01) |
| *A61K 36/11* | (2006.01) |
| *A61Q 17/04* | (2006.01) |

(52) U.S. Cl.
CPC .............. *A61K 9/1273* (2013.01); *A61K 8/14* (2013.01); *A61K 8/9741* (2017.08); *A61K 36/11* (2013.01); *A61Q 17/04* (2013.01)

(58) Field of Classification Search
None
See application file for complete search history.

(56) References Cited

U.S. PATENT DOCUMENTS

2011/0059162 A1* 3/2011 Reed ..................... A61L 29/085
424/488

OTHER PUBLICATIONS

Esposto et al., Trends Food Sci. & Tech., 2021, vol. 106, pp. 40-48 (Year: 2021).*
Shalaby et al., J. Pharm. Sci., 2018, vol. 107, pp. 2136-2143 (Year: 2018).*
Wu et al., Int. J. Biological Macromol., 2019, vol. 123, pp. 291-299 (Year: 2019).*
Stefani Esposto et al. "Liposomes vs. chitosomes: Encapsulating food bioactives". Trends in Food Science and Technology, Dec. 9, 2020, vol. 108, pp. 40-48, ISSN 0924-2244.
Ghaleshahi et al. "Influence of Sodium Alginate and Genipin on Stability of Chitosome Containing Perilla Oil in Model and Real Drink". European Journal of Lipid Science and Technology Aug. 2020, Jul. 31, 2020, vol. 122, No. 8, pages Article No. 1900358, ISSN 1438-7697(print) ISSN 1438-9312(electronic).
Ghormade et al. "Can fungi compete with marine sources for chitosan production?" International Journal of Biological Macro-molecules, Jan. 29, 2017 Elsevier BV, NL Adali Terin, Jan. 29, 2017, vol. 104, pp. 1415-1421, ISSN 0141-8130.
International Search Report for PCT/ES2021/070201 dated Nov. 26, 2021.
Menikarachchi et al. "Release behaviour of amoxicillin from chitosan coated liposomes derived from eggs". Journal of the National Science Foundation of Sri Lanka Jun. 2016, May 31, 2016, vol. 44, No. 2, pp. 167-173, ISSN 1391-4588(print) ISSN 2362-0161 (electronic).
Wu et al. "Fungal chitosan from *Agaricus bisporus*(Lange) Sing. Chaidam increased the stability and antioxidant activity of liposomes modified with biosurfactants and loading betulinic acid". International Journal of Biological Macromolecules Elsevier BV, NL Adali Terin, Feb. 15, 2019, vol. 123, pp. 291-299, ISSN 0141-8130.

* cited by examiner

*Primary Examiner* — Brian Gulledge
(74) *Attorney, Agent, or Firm* — Brown & Michaels, PC

(57) ABSTRACT

The use of nanometric liposome-like (chitosomes) in pharmaceutical or cosmetic composition and a preparation thereof with the chitosomes including chitosan molecules, phospholipid molecules, a cross-linking agent and at least one active pharmaceutical or cosmetic ingredient.

18 Claims, 2 Drawing Sheets

Figure 1:
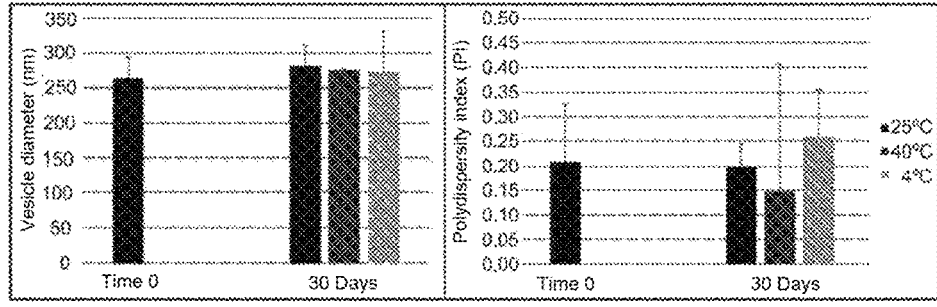

CHITOSOMES OR CHITOSAN-COATED LIPOSOMES, USE THEREOF TO OBTAIN COSMETIC OR PHARMACEUTICAL COMPOSITIONS AND PREPARATION METHOD THEREOF

OBJECT OF THE INVENTION

This invention relates to chitosomes, the use thereof in topical or oral cosmetic or pharmaceutical compositions and a preparation method thereof. More specifically, this invention relates to nanometric liposome-like vesicles (chitosomes) comprising chitosan molecules, phospholipid molecules, a cross-linking agent and at least one active pharmaceutical or cosmetic ingredient. The invention also relates to the use of chitosomes in topical cosmetic or pharmaceutical compositions and to a preparation method thereof.

Liposomes are drug delivery nanocarriers that can adhere to biomembranes and form mixed micelle structures with bile salts to increase the solubility of poorly soluble drugs. They can encapsulate hydrophilic, hydrophobic and amphiphilic compounds, and although the instability of liposomes in the gastrointestinal tract has been reported due to their low resistance to gastric pH and enzymatic degradation, they can be protected by a polymer coating.

Chitosan is a linear copolymer made up of glucosamine and N-acetylglucosamine residues and it has a strong positive charge. Chitosan exhibits valuable mucoadhesive properties that provide greater epithelial permeability by stimulating the opening of narrow junctions in the gastrointestinal tract, thus increasing paracellular transport. It has been widely reported that the chitosan coating prolongs the circulation lifetime of liposomes in the body and allows for a slower diffusion of drugs from the liposome.

In addition, the chitosan coating results in a change in particle size and a more positive zeta potential of the liposomes, forming a more stable system. Chitosan enhances the structural integrity of the liposome membrane, decreases the fluidity of the membrane, and also decreases the tendency of the liposome to aggregate, forming a conformational cloud around the liposomes that generates steric hindrance.

Chitosan is derived from chitin and numerous types exist in nature due to variations in deacetylation conditions. It is considered non-toxic and is approved for dietary use in Italy, Japan and Finland. However, the main source of commercial chitin are crustacean exoskeletons, such as shell waste from shrimp, lobsters and crabs. This means that people with shellfish allergies must be careful with shellfish-derived chitosan due to the residual reagents and antigens.

The quality of shellfish-derived chitosan depends on the conditions of the chemical extraction process, the concentration of the chemicals used, the exposure time and the deprotection, decalcification and deacetylation events.

To avoid these problems of allergic reactions, the invention proposes the use of fungi-derived chitosan, which also does not require aggressive acid treatment for its purification in order to eliminate calcium carbonate and other metals and minerals from crustacean shells.

In addition, chitin present in fungi is covalently bonded to P-glucan and fungal chitosan has a medium-low molecular weight, while that from crustaceans has a high molecular weight. Low molecular weight is generally comprised between 20 kDa and 190 kDa with a degree of deacetylation below 75%. On the contrary, high molecular weight chitosan is comprised between 190 kDa and 375 kDa with a degree of deacetylation above 75%.

The use of a suitable type of chitosan is essential for the development of encapsulation carriers for sustained drug delivery. Therefore, it is essential to keep in mind that the present patent focuses only on fungal chitosan-coated liposomes, not only due to the increased risk of allergies to conventional shellfish chitosan, but also given the fact that the properties of the polymers vary significantly depending on their origin.

Therefore, it aims to file a patent for the work performed in the laboratory and at an industrial level on liposomes that encapsulate a drug or molecule of interest, said liposomes coated with fungal chitosan cross-linked with polyanions as a resistant system in the gastrointestinal tract. Detailed descriptions of chitosomes are provided herein. It must be understood, however, that the present invention can be embodied in various ways. Therefore, the specific details described should not be interpreted as limiting, but rather as a basis for the claims and the application of the present invention in any suitable manner.

This invention will now be described by way of a non-limiting example, according to the preferred embodiments thereof, with particular reference to the figures of the accompanying drawings that show:

FIG. 1. Mean diameter (MD), polydispersity index (PI) of PL-Liposomes during 30 days of the stability test.

Figure 2:
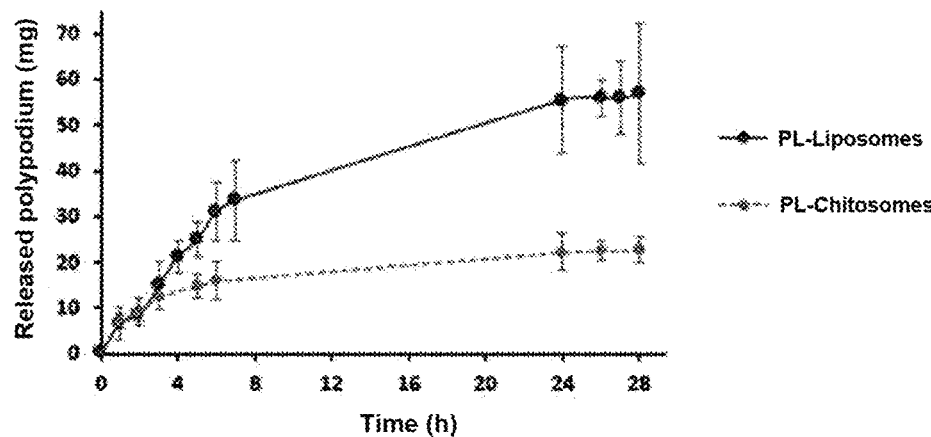

FIG. 2. Amount of PL released from PL-Solution, PL-Liposomes and PL-Chitosomes as a function of time.

Figure 3:
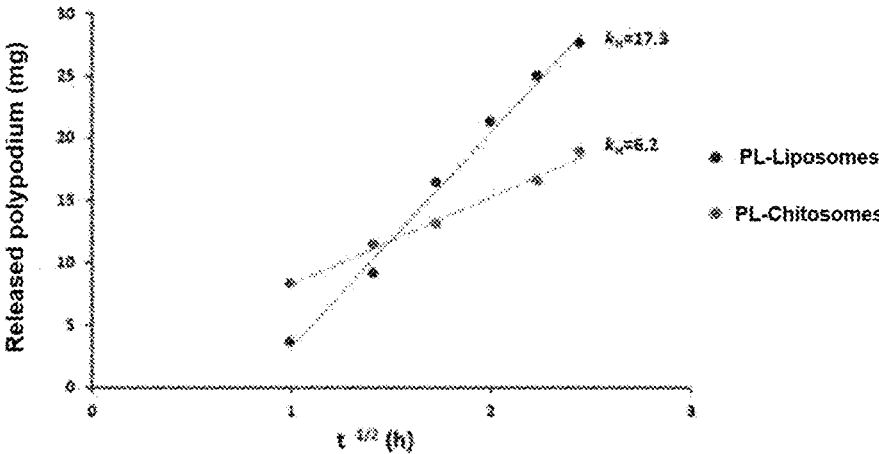

FIG. 3. Higuchi release profile of PL released from PL-Liposomes and PL-Chitosomes in simulated gastric fluid.

Figure 4:
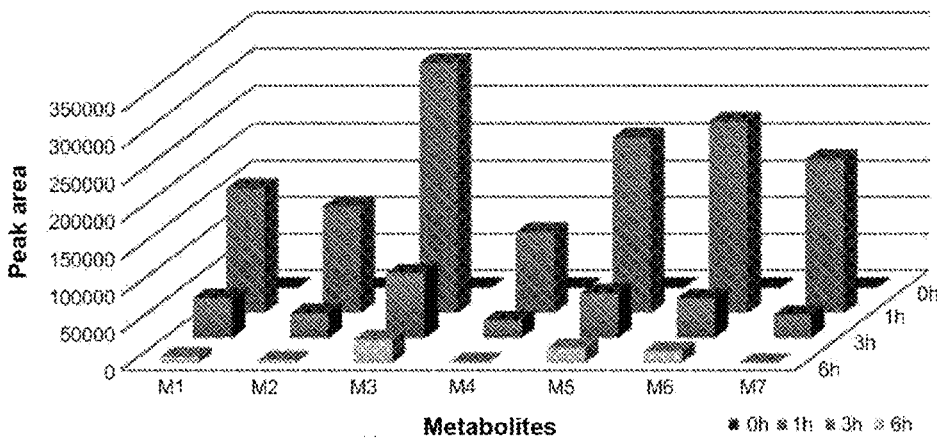

FIG. 4. Graphic representation of the peak area signal for the 7 differential metabolites detected in PL-Chitosomes, after oral intake in 10 human volunteers and blood serum collection at 0 hours (before), 1 hour, 3 hours and 6 hours after intake.

PREFERRED EMBODIMENT

In a preferred embodiment, the nanometric liposome vesicles for obtaining cosmetic or pharmaceutical compositions comprise:

a) low molecular weight fungal chitosan that is generally comprised between 20 kDa and 190 kDa and with a degree of deacetylation below 75%.

b) at least one phospholipid, from the group consisting of soy or egg lecithin, hydrogenated or non-hydrogenated phosphatidylcholine, phosphatidylethanolamine, phosphatidylserine, phosphatidylglycerol, phosphatidylinositol, dimydhatidristoylpholine (dmydiristoylpholine) (DPPC), distearoylphosphatidylcholine, palmitoyl-stearoylphosphatidylcholine, sphingomyelin, mixtures of hydrogenated and non-hydrogenated soy-derived phospholipids, preferably hydrogenated and non-hydrogenated soy phosphatidylcholine.

c) at least one active pharmaceutical or cosmetic ingredient selected from the group consisting of antivirals, proteins, vitamins and esters thereof, plant extracts or any other active ingredient.

d) at least one cross-linking agent, which is a polyanion, such as sodium tripolyphosphate, to cross-link chitosan and improve the stability of the vesicle/chitosome overtime.

In these vesicles, the phospholipid forms a double layer, the chitosan is arranged covering the double layer, with the cross-linking agent between the liposome and the chitosan to stabilize the bonds therebetween.

The vesicles can include non-ionic surfactants or co-solvents, and/or suitable modifiers, as well as cholesterol.

In these vesicles, chitosan has a concentration of 0.01% to 5%, preferably 0.02% to 2%, and at least one phospholipid has a concentration of 0.1% to 30%, preferably 0.5% to 25%, wherein said percentages are by weight of chitosan or phospholipid with respect to the weight of vesicle dispersion.

A pharmaceutical or cosmetic composition is obtained from these vesicles, for topical or oral use, said composition containing the vesicles as an active ingredient in combination with one or more pharmaceutically or cosmetically acceptable excipients or adjuvants.

Soy lecithin and polysorbate 20, or the chosen phospholipid and surfactant, are briefly dissolved in ethanol and the active molecule of interest is dissolved in the resulting mixture if it is fat-soluble or the molecules of interest are dissolved in the aqueous phase if they are water-soluble. Both phases are mixed for a specified time. A preservative solution is added to the liposomal suspension.

After that, a dispersion of chitosan in acetic acid/water is added to the liposomal dispersion to produce chitosomes. The chitosomes are further treated with a polyanion to cross-link chitosan.

More specifically, the method for preparing vesicles consists of mixing the ingredients with the following steps:

a) formation of the liposomal suspension by diluting the phospholipid and the chosen surfactant in ethanol; the active molecule is dissolved in the resulting mixture if it is fat-soluble, and the active molecules of interest that are water-soluble are dissolved in an aqueous phase, and both phases are mixed for a specified time by adding a preservative solution to the liposomal suspension;

b) formation of the chitosomes by adding a dispersion of chitosan in acetic acid/water to the liposomal dispersion of step a) to produce chitosomes;

c) treatment of the chitosomes with sodium tripolyphosphate as a cross-linking agent or with any other polyanion to cross-link chitosan.

In the method mentioned, the concentration of chitosan varies from 0.01% (w/w) to 5% (w/w), preferably being from 0.02% (w/w) to 2% (w/w) and the active pharmaceutical or cosmetic ingredient is added in a chosen concentration.

Likewise, in this method for preparing chitosomes, the chosen phospholipid is used in concentrations ranging from 0.1% (w/w) to 30% (w/w), preferably from 0.5% (w/w) to 25% (w/w).

Lastly, the method further comprises the use of non-ionic surfactants, cross-linkers or co-solvents and/or suitable modifiers.

The preparation methods avoids the use of organic solvents unlike other methods described in the literature. This means that this preparation method is more environmentally sustainable and these chitosomes are more biocompatible for this reason. In addition, in these preparation methods, the chitosomes are treated with a polyanion, sodium tripolyphosphate, to cross-link chitosan and improve the stability of the chitosome over time.

The structure of the chitosomes in this invention obtains the following advantages:

Increased solvation of the encapsulation, which triggers an effect on the dissolution kinetics and, consequently, a greater capacity of the active ingredient (especially if it is poorly soluble or insoluble) to be released and absorbed in biological media (as can be seen in Study 1).

Greater stability of the delivery system and decreased tendency to aggregate due to a change in particle size and a more positive zeta potential (as can be seen in Study 1).

Greater capacity to retain the active ingredient for more time, even when the ingredients are hydrophilic substances, since said substances are previously captured in the structured carrier and, in the case that the active molecule is lipophilic, it remains anchored to the phospholipid bilayer (as can be seen in Study 1).

Improved bioavailability compared to known vesicle or liposomal systems (as can be seen in Study 2).

To demonstrate the features and properties of the chitosomes obtained, two studies are included that are described below.

Study 1

Purpose:

To evaluate the greater capacity of chitosomes to retain the active ingredient for more time, controlled release experiments were conducted using chitosomes and liposomes that encapsulate Polypodium Leucotomos (PL) in simulated gastric fluid (SGF).

Method:

The release of PL from liposomes modified on the surface of chitosan (PL-Chitosomes) and liposomes (PL-Liposomes, uncoated vesicles) was evaluated in SGF, in order to simulate a realistic competitive environment. To that end, an equal volume of the different samples was placed in a dialysis bag and immersed in a known volume of SGF. Aliquots were taken from the external SGF at scheduled times. The release of PL was determined by following the UV intensity of chlorogenic acid (one of the main compounds of PL) in solution (Aem=340 nm). All experiments were conducted in triplicate.

Results

The PL-containing chitosomes developed in this study have a vesicle diameter in the range of 250-350 nm, with a polydispersity index below 0.5 for 30 days stored at different temperatures (25° C., 4° C. and 40° C.). The results indicated the good stability of the developed liposomes as indicated in FIG. 1, which represents the mean diameter (MD) and the polydispersity index (PI) of PL-Liposomes during 30 days of the stability test, and the zeta potential of the liposomes was positive.

The PL delivery kinetic profiles for PL-Chitosomes and PL-Liposomes in SGF are shown in FIG. 2, in which the amount of PL released from the PL solution, PL-Liposomes and PL-Chitosomes is represented as a function of time. As can be observed, no significant differences were initially observed in the PL release profile of the two types of vesicles. However, after 4 hours, the PL-Liposomes exhibited an explosive release of PL compared to the PL-Chitosomes, reaching a plateau after 24 hours. Furthermore, PL-Chitosomes maintained a sustained release of PL throughout all time points studied.

Furthermore, in addition to demonstrating the release of PL from the different vesicles, the study also aimed to evaluate the capacity of the chitosomes to maintain a controlled release of PL. To study the two different PL release profiles in greater depth, the PL release kinetics over shorter times (from 1 to 6 hours) was adjusted to the Higuchi model. The Higuchi model describes drug release as a diffusion process based on Fick's law, which depends on time from the square root of time (Equation 1). This expanded model takes into account the hypothesis that drug diffusion occurs in a single dimension and that drug diffusion is constant. This model has been widely and successfully applied to describe drug release kinetics for liposomal systems. FIG. 2 shows the fit of the model to the data, only taking into account the first hours of delivery (from 1 to 6 hours). The observed good fit of the model to the data suggests that PL delivery from both PL-Chitosomes and PL-Liposomes is essentially a diffusion process. To simplify the interpretation of data, the Higuchi release rate constant (kH) of PL from PL-Chitosomes and PL-Liposomes was calculated (see FIG. 3 showing the Higuchi release profile of PL released from PL-Liposomes and PL-Chitosomes in simulated gastric fluid). The calculations show that PL-Chitosomes have the lowest kH value, which means that the chitosomal formulation allows for a more sustained release of PL than the liposomal formulation and, therefore, it is more suitable for modulating the release of PL throughout the gastrointestinal tract.

$$f_t = k_H \sqrt{t} \qquad \text{Equation 1}$$

Study 2

Purpose:

Chitosan is a biodegradable polymer with mucoadhesive properties that provide greater epithelial permeability. Other groups have previously reported that chitosan-coated liposomes (chitosomes) exhibit longer GIT residence times. In this research, the bioavailability of Polypodium leucotomos chitosomes was demonstrated in vivo.

Method:

The protocol of this study is in accordance with the guidelines of the Scientific Committee on Consumer Safety (SCCS). First, 500 μl of blood was drawn by finger prick from each of the 10 human volunteers undergoing treatment, before oral intake of free PL solution or PL-chitosomes, and 1 hour (1 h), 3 hours (3 h) and 6 hours (6 h) after intake. Immediately after collection, serum was extracted from the blood samples by centrifugation and kept frozen at −80° C. until analysis.

The same human volunteers underwent treatment with free PL solution or PL-chitosomes, in different weeks (15 days between the group's intake of 2 samples), to reduce variability between different human volunteers.

The serum samples were processed prior to analysis by standard protein precipitation. To that end, 3 volumes of cold acetonitrile were added and the samples were kept at −20° C. for 20 minutes. After centrifugation, the supernatants were dried in a SpeedVac concentrator. Next, the residue was reconstituted to have a 1:1 solution that would be used for further analysis. The PL solution sample and PL-chitosomes were subjected to the same procedure as the serum samples.

Different dilutions (1:5, 1:20 and 1:200) were then injected. The serum samples were analyzed by UPLC-Q/ToF to obtain peak retention profiles, according to the serum levels thereof at different times. LC-Q-ToF analysis was performed using a UPLC-MS (QToF). Separation was performed using a Waters Acquity UPLC BEH C18 column (1.7 μm 2.1×100 mm) using water and acetonitrile with 0.1% formic acid as mobile phases. Mass analysis was performed in positive and full scan ESI modes obtained in a mass range from 50 to 1200 m/z.

The inclusion criteria were: relative frequency in the use of cosmetic sunscreen products; gender: male or female; age: between 25 and 65 years old; skin condition: Normal; skin phototype (Fitzpatrick): II, Ill and IV; skin type: dry, combination and oily; no participation in any clinical trial in the 15 days prior to the start of the study.

Furthermore, the exclusion criteria were: allergy or reactivity to any of the components of the product, or a product of a category similar to that tested; use of relevant pharmacological or hormonal treatment; presence of skin diseases or melanomas; anticipation of a relevant change in routine or way of life during the study period.

The results are expressed as mean±standard deviation (SD). All data were statistically analyzed using ordinary one-way ANOVA and the Student's t-test for unpaired data. Statistical significance was set at p<0.05, 95% confidence.

Results:

No volunteers showed symptoms of toxicity during the trial under the trial conditions, demonstrating that the formulation was biocompatible and there was an absence of allergic or adverse reactions.

The results indicate that there was no increase in serum metabolites after oral intake of the free PL supplement in any of the volunteers. The absence of metabolites in the serum of volunteers may be due to the low absorption profile of free PL. Furthermore, it was found that there was an increase in 7 different metabolites in the serum samples of volunteers after intake of the PL-Chitosome supplement for all volunteers included in the trial. The mean concentration for each of the metabolites in the volunteers was obtained and represented in a column bar graph, after subtracting the values obtained prior to the start of treatment.

The metabolites detected in PL-Chitosomes were classified according to their retention time and the results clearly indicate that the bioavailability of chitosome-encapsulated PL is much higher than that for PL in solution after oral intake in human volunteers. All volunteers showed the greatest increase in serum metabolites 1 hour after intake, and only a few metabolites were detected 6 hours after intake. 3 hours after intake, the levels of the 7 metabolites were also detectable, meaning that the PL-Chitosomes are still available in blood serum 3 hours after intake.

Therefore, the results show that higher levels of PL are detected in chitosomes 1 hour after oral intake, with clear levels detectable 3 hours after intake and practically no levels detectable 6 hours after intake; as shown in FIG. 4 with a graphic representation of the peak area signal for the 7 differential metabolites detected in PL-Chitosomes, after oral intake in 10 human volunteers and blood serum collection at 0 hours (before), 1 hour, 3 hours and 6 hours after intake.

Having sufficiently described the nature of the invention, as well as a preferred exemplary embodiment, it is stated for the suitable purposes that the ratios of the described components may be modified, provided that this does not imply an alteration of the essential features of the invention that are claimed below.

The invention claimed is:

1. Nanometric liposome vesicles for cosmetic or pharmaceutical compositions obtained by a method comprising the steps of:
   a) forming of a liposomal suspension by:
      dissolving a chosen phospholipid and a chosen surfactant in ethanol to form a first suspension; and
      dissolving molecules of an active pharmaceutical or cosmetic ingredient in pyrogen-free water and optionally glycerin to form a second suspension,
      mixing both the first suspension and the second suspension for a specified time to form the liposomal suspension and adding a preservative solution to the liposomal suspension;

b) forming chitosomes by adding a dispersion of chitosan in acetic acid and water to the liposomal suspension of step a); and c) treatment of the chitosomes with a polyanion to cross-link the chitosan the nanometric liposome vesicle comprising:

i) low molecular weight fungal chitosan;

ii) at least one phospholipid;

iii) at least one active pharmaceutical or cosmetic ingredient;

iv) liposome; and v) at least one cross-linking agent;

wherein the at least one phospholipid forms a double layer encapsulating the at least one active pharmaceutical or cosmetic ingredient, the low molecular weight fungal chitosan arranged to cover the double layer to form the nanometric liposome vesicles and the at least one cross-linking agent between the liposome and the low molecular weight fungal chitosan to stabilize bonds therebetween.

2. The nanometric liposome vesicles according to claim 1, wherein said at least one phospholipid is selected from the group consisting of: soy or egg lecithin, hydrogenated or non-hydrogenated phosphatidylcholine, phosphatidylethanolamine, phosphatidylserine, phosphatidylglycerol, phosphatidylinositol, dimydhatidristoylpholine (dmydiristoylpholine) (DPPC), distearoylphosphatidylcholine, palmitoylstearoylphosphatidylcholine, sphingomyelin, mixtures of hydrogenated and non-hydrogenated soy-derived phospholipids, and a mixture of hydrogenated and non-hydrogenated soy phosphatidylcholine.

3. The nanometric liposome vesicles according to claim 1, wherein the at least one active pharmaceutical or cosmetic ingredient is selected from the group consisting of: antivirals, vitamins and esters thereof, proteins, plant extracts and drugs of any other type.

4. The nanometric liposome vesicles according to claim 1, further comprises non-ionic surfactants or co-solvents, and/or suitable modifiers.

5. The nanometric liposome vesicles according to claim 1, wherein the at least one cross-linking agent is sodium tripolyphosphate or any other suitable cross- linking agent.

6. The nanometric liposome vesicles according to claim 1, wherein the low molecular weight fungal chitosan has a concentration of 0.01% to 5%, and the at least one phospholipid has a concentration of 0.1% to 30%, wherein said percentages are by weight of the low molecular weight fungal chitosan or the at least one phospholipid with respect to weight of the nanometric liposome vesicle dispersion.

7. The nanometric liposome vesicles according to claim 1, wherein the chitosan has a concentration of 0.01% (w/w) to 5% (w/w), preferably 0.02% (w/w) to 2% (w/w).

8. The nanometric liposome vesicles according to claim 1, wherein said active pharmaceutical or cosmetic ingredient is added in a concentration of 0.01% (w/v) to 30% (w/v).

9. The nanometric liposome vesicles according to claim 1, wherein said phospholipid is used in concentrations ranging from 0.1% (w/w) to 30% (w/w), preferably from 0.5% (w/w) to 25% (w/w).

10. The nanometric liposome vesicles according to claim 1, further comprising adding non-ionic surfactants, cross-linkers or co-solvents and/or suitable modifiers.

11. The nanometric liposome vesicles according to claim 6, wherein the low molecular weight fungal chitosan has a concentration of 0.02& to 2% and the at least one phospholipid has a concentration of 0.5% to 25%, wherein the percentages are by weight of the low molecular weight fungal chitosan or the at least phospholipid with respect to weight of nanometric liposome vesicle dispersion.

12. A pharmaceutical or cosmetic composition for topical or oral use comprising: an active ingredient of nanometric liposome vesicles comprising: a low molecular weight fungal chitosan; at least one phospholipid; at least one active pharmaceutical or cosmetic ingredient; liposome; and at least one cross-linking agent;

wherein the at least one phospholipid forms a double layer encapsulating the at least one active pharmaceutical or cosmetic ingredient, the low molecular weight fungal chitosan arranged to cover the double layer to form the nanometric liposome vesicles and the at least one cross-linking agent between the liposome and the low molecular weight fungal chitosan to stabilize bonds therebetween; and one or more pharmaceutically or cosmetically acceptable excipients or adjuvants.

13. The pharmaceutical or cosmetic composition according to claim 12, wherein said at least one phospholipid is selected from the group consisting of: soy or egg lecithin, hydrogenated or non-hydrogenated phosphatidylcholine, phosphatidylethanolamine, phosphatidylserine, phosphatidylglycerol, phosphatidylinositol, dimydhatidristoylpholine (dmydiristoylpholine) (DPPC), distearoylphosphatidylcholine, palmitoylstearoylphosphatidylcholine, sphingomyelin, mixtures of hydrogenated and non-hydrogenated soy-derived phospholipids, and a mixture of hydrogenated and non-hydrogenated soy phosphatidylcholine.

14. The pharmaceutical or cosmetic composition according to claim 12, wherein the at least one active pharmaceutical or cosmetic ingredient is selected from the group consisting of: antivirals, vitamins and esters thereof, proteins, plant extracts and drugs of any other type.

15. The pharmaceutical or cosmetic composition according to claim 12, further comprises non-ionic surfactants or co-solvents, and/or suitable modifiers.

16. The pharmaceutical or cosmetic composition according to claim 12, wherein the at least one cross-linking agent is sodium tripolyphosphate or any other suitable cross-linking agent.

17. The pharmaceutical or cosmetic composition according to claim 12, wherein the low molecular weight fungal chitosan has a concentration of 0.01% to 5%, and the at least one phospholipid has a concentration of 0.1% to 30%, wherein said percentages are by weight of the low molecular weight fungal chitosan or the at least one phospholipid with respect to weight of the nanometric liposome vesicle dispersion.

18. The pharmaceutical or cosmetic composition according to claim 17, wherein the low molecular weight fungal chitosan has a concentration of 0.02& to 2% and the at least one phospholipid has a concentration of 0.5% to 25%, wherein the percentages are by weight of the low molecular weight fungal chitosan or the at least phospholipid with respect to weight of nanometric liposome vesicle dispersion.

* * * * *